(12) United States Patent
Jockel et al.

(10) Patent No.: US 7,399,705 B2
(45) Date of Patent: Jul. 15, 2008

(54) METHOD FOR PRODUCING A LOCAL COATING AND COMBINATORY SUBSTRATE HAVING SUCH COATING

(75) Inventors: Jörg Jockel, Gerlingen (DE); Andreas Müller, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 327 days.

(21) Appl. No.: 11/182,371

(22) Filed: Jul. 15, 2005

(65) Prior Publication Data
US 2006/0019413 A1 Jan. 26, 2006

(30) Foreign Application Priority Data
Jul. 15, 2004 (DE) .................. 10 2004 034 078

(51) Int. Cl.
*H01L 21/44* (2006.01)
(52) U.S. Cl. ..................... 438/676; 438/5; 438/674; 257/E21.171

(58) Field of Classification Search ............ 438/5, 438/758, 678, 785, 674, 676
See application file for complete search history.

(56) References Cited

U.S. PATENT DOCUMENTS

| 6,996,550 B2 * | 2/2006 | Wang et al. ............... 706/19 |
| 2005/0048205 A1 * | 3/2005 | Woo et al. ............... 427/248.1 |

* cited by examiner

*Primary Examiner*—Alexander G Ghyka
(74) *Attorney, Agent, or Firm*—Kenyon & Kenyon LLP

(57) ABSTRACT

A method for producing at least one local coating on a substrate is provided, as well as a combinatory substrate having such a local coating, a mask that is removable in a non-destructive manner being arranged on the substrate in a first step; the mask having at least one perforation, the perforation being at least partially filled with a reactive solution in a second step; and a coating reaction of the reactive solution with the substrate surface being induced in a third step to form the local coating.

8 Claims, 2 Drawing Sheets

METHOD FOR PRODUCING A LOCAL COATING AND COMBINATORY SUBSTRATE HAVING SUCH COATING

BACKGROUND INFORMATION

The present invention relates to a method and a device for producing and testing composite systems.

The discovery and development of new substances and materials is a primary goal of the material sciences, of chemistry and the science of pharmacology. However, the search for suitable compounds is often very costly and time-consuming. To be able to conduct this search more effectively and inexpensively, a systematic methodology, which has become known as "combinatory chemistry", was introduced in the pharmaceutical and then also in other application fields quite a few years ago. Here, several potentially interesting compounds are produced and analyzed quasi in parallel. The advantage of this method is that it allows automation, so that high processing speeds are possible in a minimum of time.

The basis of this method is the use of substrates on which a multitude of chemical compounds that may possibly have a useful property are applied spatially separate from each other. In some cases the production of such substrates constitutes a challenge. For instance, if possible materials for electrodes are to be tested with the aid of a combinatory substrate, the corresponding electrodes are galvanically deposited by hand or anodically oxidized according to the deposition methods currently in use.

For each electrode material to be deposited, the entire substrate is immersed in a corresponding electroplating dip, the substrate is electrically contacted at least in the region of the electrode material to be deposited, and a sufficient quantity of the metallic electrode material is deposited by applying a corresponding galvanic voltage between substrate and electroplating dip. To obtain electrodes of the second type, anodic oxidation of the deposited electrode material in an appropriate metallic salt solution may be carried out in addition. In a final step, the substrate is taken out of the electroplating dip, and a rinsing operation is implemented. The number of the various electrode materials provided on a substrate is thus equal to the number of individual deposition operations that must be carried out.

It is an object of the present invention to provide a method and a device that allow the production of local coatings on a substrate in an effective and thus inexpensive manner.

SUMMARY

An example method and the device according to the present invention may have the advantage that a plurality of local coatings on the basis of different materials may be produced on a substrate simultaneously and in a simple manner. In a first step, a mask which is able to be removed without being destroyed and which has at least one perforation, is arranged on the substrate. In a second step, the perforations of the mask are at least partially filled with different reaction solutions suitable for producing the individual local coating, and a coating reaction of the reactive solutions with the substrate surface is induced in a third step while the particular coatings are formed. This makes it possible to produce a large number of different local coatings on a substrate in a simultaneous manner.

To induce the coating reaction, it may be advantageous, for instance, if electrically conductive layers in the form of electrodes are first deposited at the positions of the substrate to be coated, and a galvanic voltage is applied between these and an additional electrode or the reactive solution. As an alternative or in addition, an anodic voltage may be applied in an advantageous manner.

In an especially advantageous embodiment of the present method, a simultaneous contacting of a plurality of conductive layers deposited on the substrate, which is required prior to the galvanic deposition of the coating, takes place. An advantageous alternative approach is to implement the contacting of the conductive layers sequentially with the aid of a moveable contact pin which triggers and contacts contact points of the individual conductive layers one after the other.

In order to be able to test the suitability of the deposited materials with respect to their possible function as measuring electrodes of an electrochemical gas sensor, it may be advantageous if the electrode materials deposited in the form of local coatings as measuring electrodes are contacted, and if a reference electrode is deposited on the backside of the substrate, for instance, so that a potential difference between the reference potential of the reference electrode and the potential coming about at the individual electrode materials is able to be determined.

In an advantageous manner, the substrate used for this purpose, on which at least two defined points are located where a material is to be deposited in each case, has at least one means for the electrical contacting of the corresponding locations of the substrate so that the materials deposited on the substrate are electrically addressable.

BRIEF DESCRIPTION OF THE DRAWINGS

An exemplary embodiment of the method according to the present invention is shown in the drawing and explained in greater detail below.

FIG. 2b shows an enlargement of a cut-away portion of FIG. 2a.

DESCRIPTION OF EXAMPLE EMBODIMENTS

One idea on which the present invention is based is to extend the methodology of parallel synthesis and testing of various potentially interesting substances to research areas in which investigating the properties of individual materials by itself will not achieve the goal, but only tests on arrangements made up of two or more components will render meaningful results. Among others, this is the case in the field of sensor technology. Using the conventional methods, for instance, a metallic compound may indeed be tested with respect to its conductivity. However, whether this compound is suitable for a measuring electrode of a sensor, can be adequately tested only once the metallic compound is produced and tested in combination with a counter electrode, for instance.

Figure 1:
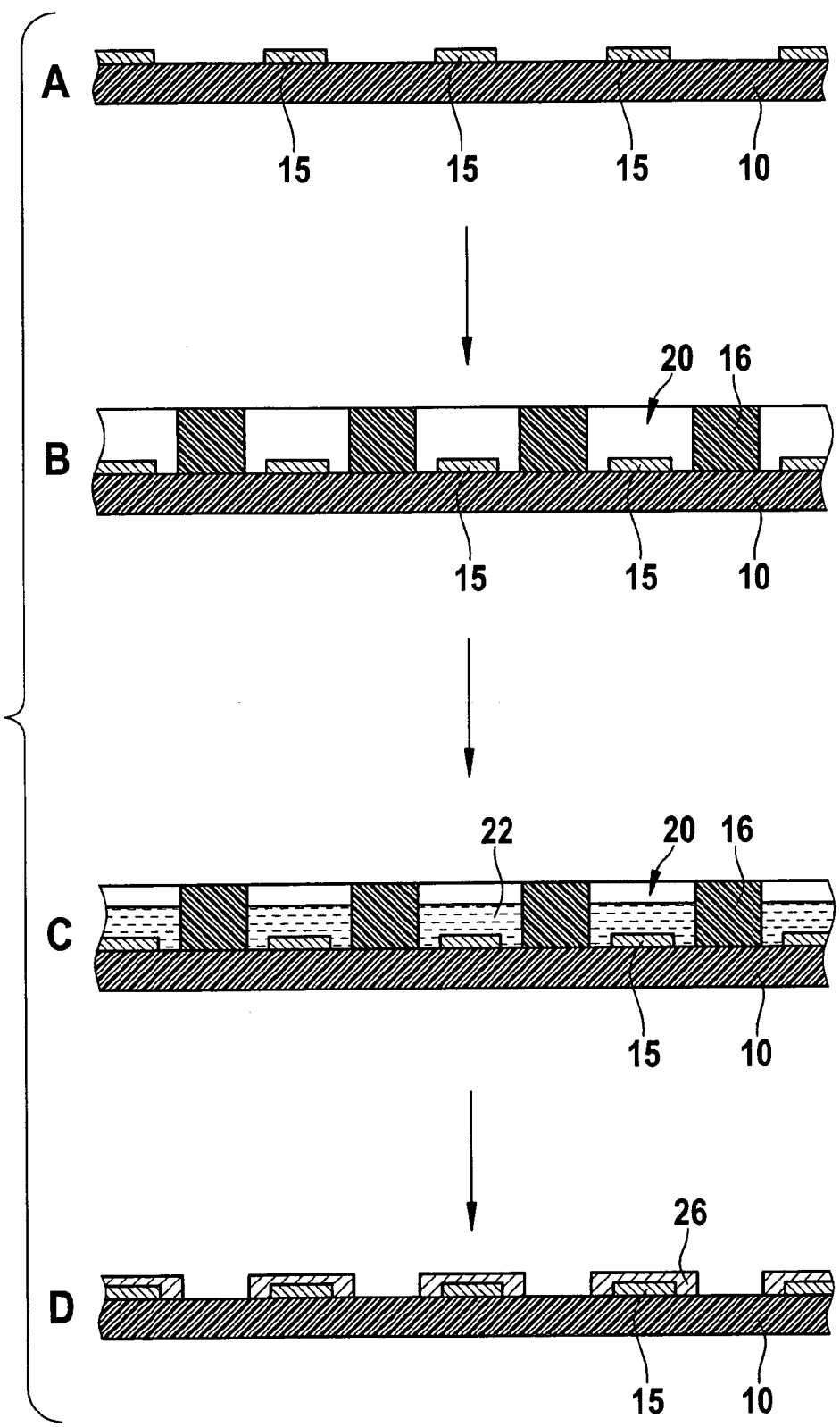
FIG. 1 shows a schematic representation of the individual method steps for the deposition of local coatings.

FIG. 1 schematically shows the individual working steps of a method for producing a substrate provided with local coatings. The local coatings may be in the form of, for instance, potential electrode materials for sensor applications.

In a first working step A, using an appropriate method, a substrate 10, which is made of a ceramic material or a suitable polymer, for instance, is provided with electrically conductive coatings in the form of electrodes 15 that are preferably made of the same metallic material. Electrodes 15 are electrically contacted with the aid of circuit traces (not shown).

Counter electrodes, which are not shown and preferably made of the same material as electrodes 15, are deposited adjacent to electrodes 15.

In a second working step B, a mask 16, which is able to be removed again later without being destroyed in the process, is reversibly placed on substrate 10. Mask 16 has perforations 20 and is positioned on substrate 10 in such a way that electrodes 15 are located in the region of perforations 20 and are freely accessible. In form and size, perforations 20 are designed such that one electrode 15 and the associated counter electrode are openly accessible within individual perforation 20. The placing of mask 16 on substrate 10 is preferably implemented in such a way that a fluid filled into perforations 20 is unable to escape via a gap between mask 20 and substrate 10. Mask 16 is made of a chemically inert material such as PVC.

In a third working step C, each perforation 20 is filled with a reactive solution 22 that fills individual perforation 20 at least partially and covers electrode 15 completely. The metering and deposition may be carried out with the aid of the usual methods, for instance by a dispenser. In the process each perforation 20 is supplied with a reactive solution that differs from the reactive solutions 22 supplied to the other perforations 20 in its material composition with respect to the dissolved substances and/or their concentration in the solution. Supplied reactive solutions 22 are preferably suitable electroplating dips.

After reactive solutions 22 have been introduced into perforations 20, electrodes 15 and possibly their counter electrodes are electrically contacted by individual contact electrodes, preferably at the associated circuit traces.

To deposit local coatings 26, a galvanic potential is applied between electrodes 15 and the individual counter electrodes. It is possible to provide an identical galvanic potential for all perforations 20. In this case, the simultaneous application of a plurality of contact electrodes suggests itself for the contacting of electrodes 15 or their counter electrodes. However, it is preferred that an individually determined galvanic potential, oriented to the deposition potential of electrode material 26 provided as local coating, be applied to each filled-in reactive solution 22. In this case the use of moveable contact pins for the contacting of electrodes 15 or their counter electrodes is especially advantageous.

An alternative is to successively dip a contact electrode or a moveable contact pin into each reactive solution filled into perforations 20 so as to contact the individual reactive solutions 22, or to successively dip a moveable contact pin into each of the filled-in reactive solutions. The immersed contact electrodes or the immersed contact pin is used in place of counter electrodes for the electrical contacting of reactive solutions 22 embodied as electroplating dip.

If substrate 10 is made of a material that conducts the electrical current, or if it is made of a semiconductor material, it is also possible to dispense with the deposition of counter electrodes to electrodes 15 on substrate 10. In this case an insulating intermediate layer should be provided between substrate 10 and electrode 15. A galvanic potential will then be applied between electrode 15 and substrate 10. Another possibility is to apply the galvanic potential between substrate 10 and the contact electrodes dipping into reactive solution 22 or the contact pins. Neither electrodes 15 nor associated counter electrodes will be required in this case.

As an alternative, it is possible to deposit local coatings 26 in a currentless manner. Corresponding reactive solutions 22 which result in a deposition of local coatings 26 when a suitable reducing agent is added, are used to this end. The use of electrodes 15 or the counter electrodes will not be required.

In addition, it is possible to produce local coatings 26 from a material that contains a catalytically active substance in most finely dispersed form.

After the electrode materials have been deposited, remaining reactive solutions 22 are siphoned off and mask 16 removed in a fourth working step D. Finally, it is preferred that a rinsing operation take place, for instance using demineralized water.

Figure 2A:
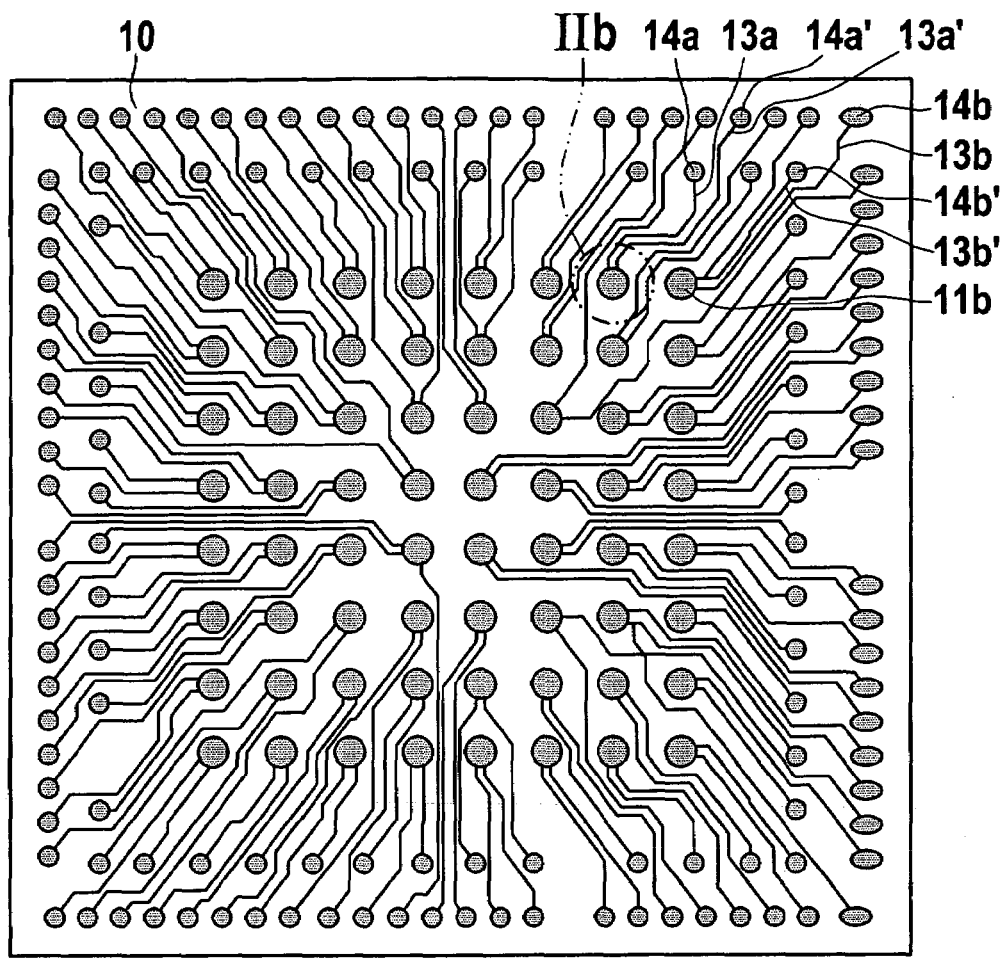
FIG. 2a shows a schematic plan view of a substrate having local coatings in the form of electrode materials that were deposited according to the method shown in FIG. 1.
Figure 2B:
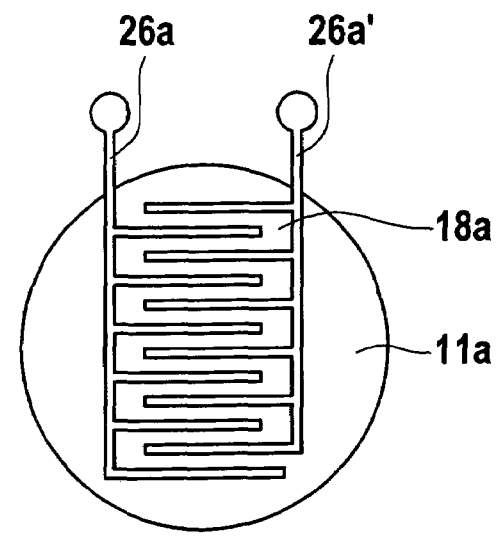

FIGS. 2a and 2b show a substrate 10 provided with coatings 26 by way of example. At at least one location 11a whose exact position on the substrate is known, substrate 10 has a local coating 26 in the form of an electrode 26a. Furthermore, a counter electrode 26a' is preferably provided at location 11a, which forms a composite arrangement together with electrode 26a and shared substrate 10 and possibly additional components. The composite arrangements produced in cohesive form in this manner are then subjected to testing with respect to a selected property.

A substrate 10, which has an electrically insulating effect and is largely made of high-ohmic materials such as aluminum oxide or silicon coated by silicon dioxide, is used for this purpose. At defined locations 11a, 11b, . . . , preferably one electrode pair 26a, 26a', 26b, 26b', . . . , is deposited on substrate 10 in each case, for instance in the form of interdigital electrodes shown in FIG. 2b in an enlargement of the cut-away portion. As schematically shown more clearly in FIG. 2a, these are connected to contact points 14a, 14a', 14b, 14b', . . . at the edge of substrate 10 by separate circuit traces 13a, 13a', 13b, 13b', . . . . Contact points 14a, 14a', 14b, 14b' . . . may basically also be arranged on the backside of substrate 10 and be contacted with the aid of a bore hole.

Finally, circuit traces 13a, 13a', 13b, 13b' . . . are preferably covered by one or a plurality of different inert layers (not shown). As an option, resistance layers 18a, 18b, . . . are additionally provided in the regions between electrodes 26a, 26a', 26b, 26b', . . . , the resistance layers possibly also covering associated electrodes 26a, 26a', 26b, 26b'.

However, it is not mandatory that two electrodes 26a, 26a', 26b, 26b' . . . be provided at each location 11a, 11b, . . . and be implemented as interdigital electrodes. It is also possible to deposit only one electrode 26a, 26b . . . at each location 11a, 11b . . . and perhaps provide a shared reference electrode, for instance on the backside of substrate 10.

To test electrode materials 26 with respect to their suitability for sensor applications, for example, a current is applied to electrodes 26a, 26a', 26b, 26b', . . . , which leads to a measurable voltage drop between electrodes 26a, 26a', 26b, 6b', . . . . The testing of electrode materials 26 with respect a desired characteristic is carried out under the action of an external stimulus. In the most general terms, this may be understood as the direct contact of electrode materials 26 with a medium that reciprocally interacts with them in a physical or chemical manner. In the case at hand, this is preferably understood as the action of gases, in particular those gases that are meant to be detected by the sensor to be developed.

The number of locations 11a, 11b, . . . to be provided on substrate 10 may be variable. It depends on practical considerations. For instance, if the number of locations is less than 16, the advantages of parallel synthesis and testing of local coatings are barely apparent anymore, whereas an upper limit is given only by a sufficiently effective administration of the obtained data quantity and coverage of the substrate surface by circuit traces 13a, 13a', 13b, 13b', or inert layers 18a, 18b, . . . that is still just sufficiently exact. Experience has shown that a manageable number of locations 11a, 11b, . . . is 256.

Among others, oxygen, nitrogen oxides, sulphur oxides, carbon monoxide, hydrocarbons, ozone, ammonia, hydrogen and hydrogen sulphide should be mentioned as gas components that are able to be determined with the aid of described substrate 10 covered by electrode materials 26. Furthermore, using the described substrate, electrode materials intended for fluid media are also able to be examined with regard to a desired property. Here, substrate 10 covered by electrode materials 26 is dipped into a suitable analyte solution into which a corresponding reference electrode is dipped as well. If the reference electrode and respective electrode materials 26 are connected to an appropriate current or voltage source, it is possible to determine the quality of the measuring signals obtained for individual electrode materials 26 when carrying out corresponding voltammetric or polarographic concentration determinations in the submitted test solution.

If an anodic oxidation of electrode materials 26 takes place during the production process, electrode materials 26 are converted into electrodes of the second type, for instance. Electrodes of the second type are electrodes that dip into a sparingly soluble salt of the particular metal of which they are made. These electrodes exhibit a largely constant potential for as long as a solid solute of the sparingly soluble salt is present. Anodically oxidized electrode materials thus allow the development of electrodes that are suitable as reference electrodes, for example.

However, the described method and the described substrate are not limited to the deposition and testing of electrode materials. Instead, the method also allows the production and testing of, for instance, potentially catalytically active layers, conductive polymers or enzymatically or immunologically active coatings.

What is claimed is:

1. A method for producing at least one local coating on a substrate, comprising:
    arranging a removable mask on the substrate, the mask being removable in a non-destructive manner, and the mask having at least one perforation;
    at least partially filling the perforation with a reactive solution; and
    inducing a coating reaction of the reactive solution with a surface of the substrate to form the local coating;
    wherein:
        the substrate is provided with a first electrically conductive layer and a second electrically conductive layer;
        an electrode, embodied as a moveable contact pin, electrically contacts the first and second electrically conductive layers one after another to induce the coating reaction;
        a galvanic voltage is applied to the electrode; and
        the galvanic voltage is applied between at least one of: i) the electrically conductive layers and the substrate, and ii) the electrically conductive layers and an additional electrode.

2. The method as recited in claim 1, wherein the local coating is an electrode.

3. The method as recited in claim 1, wherein at least two local coatings that differ in their composition are produced on the substrate, the mask has at least two perforations, and in the at least partially filling step, each of the perforations is filled with a reactive solution that differs from one another in material composition.

4. The method as recited in claim 1, wherein, after the inducing step, an anodic voltage is applied between the at least one of i) the electrically conductive layers and the substrate, and ii) the electrically conductive layers and the additional electrode.

5. A method for producing at least one local coating on a substrate, comprising:
    arranging a removable mask on the substrate, the mask being removable in a non-destructive manner, and the mask having at least one perforation;
    at least partially filling the perforation with a reactive solution; and
    inducing a coating reaction of the reactive solution with a surface of the substrate to form the local coating;
    wherein:
        an electrode, embodied as a moveable contact pin, electrically contacts, one after another, first and second electrically conductive layers with which the substrate is provided to induce the coating reaction;
        at least one of a galvanic voltage and an anodic voltage is applied between at least one of: i) the electrically conductive layers and the substrate, and ii) the electrically conductive layers and an additional electrode; and
        the at least one of the galvanic and anodic voltage is applied to the electrode.

6. The method as recited in claim 5, wherein the galvanic voltage is applied between the at least one of: i) the electrically conductive layers and the substrate, and ii) the electrically conductive layers and the additional electrode, and, after the inducing step, the anodic voltage is applied between the at least one of: i) the electrically conductive layers and the substrate, and ii) the electrically conductive layers and the additional electrode.

7. A method for producing at least one local coating on a substrate, comprising:
    arranging a removable mask on the substrate, the mask being removable in a non-destructive manner, and the mask having at least one perforation;
    at least partially filling the perforation with a reactive solution; and
    inducing a coating reaction of the reactive solution with a surface of the substrate to form the local coating;
    wherein, to induce the coating reaction:
        an electrode, embodied as a moveable contact pin, electrically contacts, one after another, first and second electrically conductive layers with which the substrate is provided to induce the coating reaction;
        a galvanic voltage is applied between at least one of: i) the electrically conductive layers and the substrate, and ii) the electrically conductive layers and an additional electrode; and
        the galvanic voltage is applied to the electrode.

8. The method as recited in claim 7, further comprising:
    subsequent to the inducing step, applying an anodic voltage between the at least one of: i) the electrically conductive layers and the substrate, and ii) the electrically conductive layers and the additional electrode, wherein the anodic voltage is applied to the electrode.

* * * * *